United States Patent [19]

Haslanger et al.

[11] Patent Number: 4,889,874
[45] Date of Patent: Dec. 26, 1989

[54] HYDROXAMIC ACID DERIVATIVES AND METHOD OF USING SAME

[75] Inventors: Martin F. Haslanger, Ridgewood; Eric M. Gordon, Pennington, both of N.J.

[73] Assignee: E. R. Squibb & Sons, Inc., Princeton, N.J.

[21] Appl. No.: 183,406

[22] Filed: Mar. 14, 1988

Related U.S. Application Data

[63] Continuation of Ser. No. 883,227, Jul. 7, 1986, abandoned.

[51] Int. Cl.$^4$ ..................... C07C 83/10; A61K 73/185
[52] U.S. Cl. ..................................... 514/575; 562/622
[58] Field of Search ................. 260/500.5 H; 514/575; 562/622

[56] References Cited

U.S. PATENT DOCUMENTS

| | | | |
|---|---|---|---|
| 3,209,026 | 9/1965 | Finkelstein et al. | 260/500.5 H |
| 3,544,583 | 12/1970 | Burk et al. | 260/500.5 H |
| 3,560,519 | 2/1971 | Burk, Jr. et al. | 260/500.5 H |
| 3,697,588 | 10/1972 | Vincent et al. | 260/500.5 H |
| 3,746,751 | 7/1973 | Noguchi et al. | 260/500.5 H |
| 3,857,946 | 12/1974 | Shibata | 424/266 |
| 3,900,514 | 8/1975 | Chappelow et al. | 260/500.5 H |
| 3,936,494 | 2/1976 | Lipowski | 260/500.5 H |

FOREIGN PATENT DOCUMENTS

0127726 1/1984 European Pat. Off. .

OTHER PUBLICATIONS

Fieser et al, "Organic Chemistry", 3rd ed. (1956) pp. 97 and 98.

*Primary Examiner*—J. E. Evans
*Attorney, Agent, or Firm*—Theodore R. Furman, Jr.

[57] ABSTRACT

In accordance with the present invention, new hydroxamic acid derivatives useful as $\Delta^5$-lipoxygenase inhibitors are provided. These new compounds have the general formula

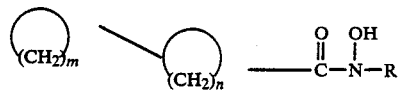

wherein

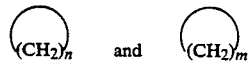

are cycloalkyl groups which may be the same or different; R is hydrogen, lower alkyl, aryl, lower alkenyl, cycloalkyl or aralkyl; n is an integer from 3 to 12; and m is an integer from 3 to 12. Further in accordance with the present invention, a method for using the above compounds is provided.

11 Claims, No Drawings

HYDROXAMIC ACID DERIVATIVES AND METHOD OF USING SAME

This is a continuation of co-pending application Ser. No. 883,227 filed on July 7, 1986 now abandoned.

FIELD OF THE INVENTION

The present invention relates to hydroxamic acid derivatives and more particularly concerns such derivatives which are inhibitors of $\Delta^5$-lipoxygenase and as such are useful, for example, as antiallergy agents.

BACKGROUND OF THE INVENTION

U.S. Pat. No. 3,560,519 to Burk et al. discloses aromatic monohydroxamic acids of the general formula

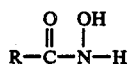

wherein R is an aromatic hydrocarbon radical of 1 to 3 aromatic rings with the proviso that when R is monocyclic it contains as a substituent one or more halogen or alkoxy groups.

U.S. Pat. No. 3,857,946 to Shibota discloses hydroxamic acid derivatives of the general formula

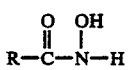

wherein R is alkyl, substituted or unsubstituted aryl or pyridyl. These compounds are useful as addition agents to improve feed for domestic animals and poultry.

European patent application No. 0,127,726 to Schewe discloses the hydroxamic acids of the formula

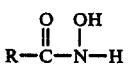

wherein R is

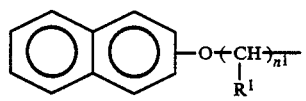

These compounds have been found useful as $\Delta^5$-lipoxygenase inhibitors.

Novel compounds having activity as $\Delta^5$-lipoxygenase inhibitors would be a useful addition to the art.

SUMMARY OF THE INVENTION

In accordance with the present invention, new hydroxamic acid derivatives useful as $\Delta^5$-lipoxygenase inhibitors are provided. These new compounds have the general formula

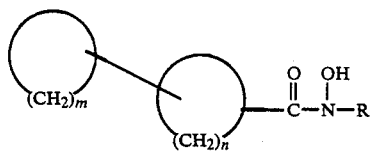

wherein

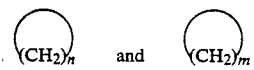

are cycloalkyl groups which may be the same or different; R is hydogen, lower alkyl substituted alkyl, aryl substituted aryl, lower alkenyl, cycloalkyl, or aralkyl; n is an integer from 3 to 12; and m is an integer from 3 to 12. Further in accordance with the present invention, a method for using the above compounds is provided.

DETAILED DESCRIPTION OF THE INVENTION

The hydroxamic acid derivatives of the present invention may form salts with alkali metals, such a lithium, sodium or potassium. In addition, the compounds of formula I will form salts with dicyclohexylamine or other amines as well as with tris(hydroxymethyl)aminomethane, glucamine and other amines as set out in U.S. Pat. No. 4,294,759.

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl or dodecyl. The term "substituted alkyl" as employed herein refers to an alkyl group as described above including a halo-substituent selected from F, Br, Cl or I or $CF_3$, an alkoxy substituent, an alkyl-aryl substituent, a haloaryl substituent, a cycloalkyl substituent, an alkylcycloalkyl substituent, hydroxy, an alkylamino substituent, an alkanoylamino substituent, an arylcarbonylamino substituent, a nitro substituent, a cyano substituent, a thiol substituent or an alkylthio substituent.

The term "cycloalkyl" employed herein by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, which groups are substituted with the same, or a different cycloalkyl, preferably at the 2, 3 or 4 position.

The term "aryl" or "Ar" as employed herein by itself or as part of another group refers to monocyclic or bicyclic aromatic groups containing from 6 to 10 carbons in the ring portion, such as phenyl or naphthyl.

The term "substituted aryl" refers to substituted phenyl or substituted naphthyl wherein the substituent on either the phenyl or naphthyl may be 1 or 2 halogens selected from chlorine, bromine or fluorine, 1 or 2 lower alkoxy groups, 1 or 2 hydroxyl groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

The term "aralkyl", "aryl-alkyl" or "aryl-lower alkyl" as used herein refers to lower alkyl groups as discussed above having an aryl substituent, such as benzyl.

The term "lower alkenyl" or "alkenyl" as employed herein by itself or as part of another group includes an unsaturated hydrocarbon group having from 3 to 8 carbons and a single carbon-carbon double bond, such as ethenyl, 1-propenyl, 2-propenyl, 1-butenyl, 2-butenyl, 3-butenyl and the like.

The term "lower alkoxy" as employed herein includes the above-defined lower alkyl group linked to an oxygen atom.

The term "acyl" as used herein by itself or as part of another group refers to an alkyl carbonyl or alkenyl carbonyl group.

The term "aroyl" as used herein by itself or as part of another group refers to an aryl carbonyl group.

The term "halogen" or "halo" as used herein refers to chlorine, bromine, fluorine or iodine with chlorine being preferred.

Preferred are those compounds of the invention wherein

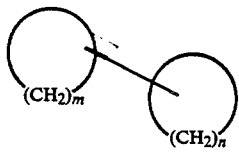

is 4-cyclohexylcyclohexyl and R is lower alkyl, such as methyl or ethyl.

The various compounds of the invention may be prepared as described below.

A carboxylic acid of the formula

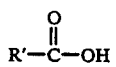
II (wherein R' is an aromatic hydrocarbon substituted with the same, or a different, aromatic hydrocarbon) is put into a solution with an appropriate organic solvent, e.g., ethanol, an acid such as acetic acid or propionic acid, with or without the presence of a trace of a mineral acid, e.g., hydrochloric or sulfuric, and platinum oxide. This solution is first hydrogenated at, or above, atmospheric pressure and at a temperature between about 20° and 100° C., to afford a compound of the formula

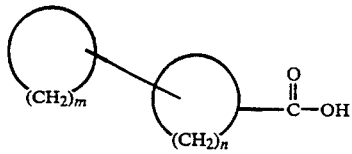
III

Thereafter, the acid of formula III in a solvent, e.g., tetrahydrofuran, is subjected to a chlorinating agent, e.g., oxalyl chloride or thionyl chloride, to give the acid chloride of the formula

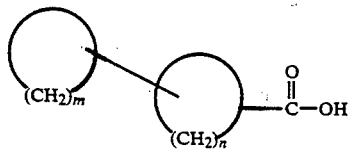
IV.

Compound IV is then reacted with one or more parts of an amine of the formula

V to provide the compound of formula I.

The compounds of the invention are $\Delta^5$-lipoxygenase inhibitors and prevent leukotriene $C_4$ formation in macrophages (Samuelsson, B., Science, Vol. 220, p. 568–575, 1983). The administration of compounds of this invention to humans or animals provides a method for treating allergy of a reagin or non-reagin nature. Asthma is preferably treated but any allergy wherein leukotrienes are thought to be involved as pharmacological mediators of anaphylaxis can be treated. For example, the compounds of this invention can be used for treatment of such conditions as allergic rhinitis, food allergy and urticaria as well as asthma.

An effective but essentially non-toxic quantity of the compound is employed in treatment.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional manner with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following examples represent specific embodiments of the present invention.

EXAMPLE 1

4-Cyclohexyl-N-hydroxy-N-methylcyclohexanecarboxamide

A. 4-Cyclohexyl-cyclohexane-carboxylic acid

A solution of biphenyl-4-carboxylic acid (9.9 g, 50 mmol) in 500 ml of ethanol and 150 ml of glacial acetic acid containing 1.0 g of platinum oxide was hydrogenated overnight at 40 psi. Upon filtering the solution and concentrating the filtrate under reduced pressure, 10.5 g of bicyclohexyl-4-carboxylic acid was obtained as a white solid (m.p. 122°–125° C.).

B. 4-Cyclohexyl-N-hydroxy-N-methylcyclohexane-carboxamide

To a solution of 4-cyclohexyl-cyclohexanecarboxylic acid (1.47 g, 7 mmol) in 50 ml of tetrahydrofuran was added oxalyl chloride (0.67 ml, 7.7 mmol) and a few drops of dimethylformamide. After stirring for one hour, the reaction mixture was concentrated to about ⅓ of the original volume and added dropwise into a cold (~0° C.), stirred solution of N-methylhydroxylamine hydrochloride (1.17 g, 14 mmol) in 40 ml of 1N sodium hydroxide. The mixture was stirred for two hours and extracted three times with ethyl acetate. The combined ethyl acetate extracts were washed twice with water, dried with anhydrous sodium sulfate and concentrated. Purification by flash chromatography and crystallization afforded 0.342 g of 4-cyclohexyl-N-hydroxy-N-methylcyclohexanecarboxamide as a white solid (m.p. 89°–90° C.).

EXAMPLE 2

4-Cyclohexyl-N-(1,1-dimethylethyl)-N-hydroxycyclohexanecarboxamide

A. 4-Cyclohexyl-cyclohexane-carboxylic acid

The 4-cyclohexyl-cyclohexane-carboxylic acid was prepared as in part A of Example 1.

B. 4-Cyclohexyl-N-(1,1-dimethylethyl)-N-hydroxy-cyclohexanecarboxamide

To a solution of 4-cyclohexyl-cyclohexanecarboxylic acid (1.47 g, 7 mmol) in 20 ml of tetrahydrofuran was added oxalyl chloride (0.67 ml, 7.7 mmol) and a few drops of dimethylformamide. After stirring for one hour, the reaction mixture was added dropwise into a cold (~0° C.), stirred solution of N-(1,1-dimethylethyl)-hydroxylamine hydrochloride (1.75 g, 14 mmol) in 40 ml of 1N sodium hydroxide. The mixture was stirred for two hours, from 0° C. to room temperature and extracted three times with ethyl acetate. The combined ethyl acetate extracts were then washed twice with water, dried with anhydrous sodium sulfate and concentrated. Purification by flash chromatography provided 0.186 g of the 4-cyclohexyl-N-(1,1-dimethylethyl)-N-hydroxy-cyclohexane-carboxamide as a white solid (m.p. 119°–120° C.).

EXAMPLES 3 TO 20

The following additional compounds within the scope of the present invention may be prepared employing the teachings as outlined above and in the working Examples.

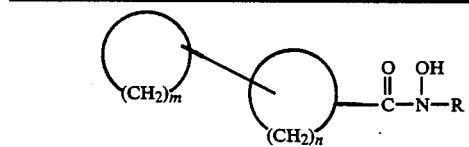

| Example No. | $(CH_2)_m$ ring | $(CH_2)_n$ ring | R |
|---|---|---|---|
| 3 | 6-ring | 6-ring (4,1) | H |
| 4 | 6-ring | 5-ring (3,1) | $C_2H_5$ |
| 5 | 5-ring | 6-ring (4,1) | $CH_3-CH(CH_3)-$ |
| 6 | 6-ring | 6-ring (3,1) | phenyl |
| 7 | 4-ring | 5-ring (3,1) | $CH_2-CH=CH_2$ |
| 8 | 5-ring | 5-ring (3,1) | 6-ring |
| 9 | 6-ring | 6-ring (4,1) | phenyl-$C_2H_5$ |
| 10 | 7-ring | 5-ring (3,1) | $C_2H_5$ |
| 11 | 5-ring | 7-ring (4,1) | $CH_3$ |
| 12 | 6-ring | 4-ring (3,1) | $C_3H_7$ |
| 13 | 5-ring | 4-ring (3,1) | $C_7H_{15}$ |
| 14 | 6-ring | 6-ring (2,1) | $C_2H_5$ |
| 15 | 5-ring | 5-ring (2,1) | $CH_3$ |
| 16 | 6-ring | 5-ring (3,1) | $CH_2-CH_2-CH_2-C(CH_3)_3$ |
| 17 | 5-ring | 4-ring (3,1) | $OCH_3$ |

| | -continued | |
|---|---|---|
| 18 | 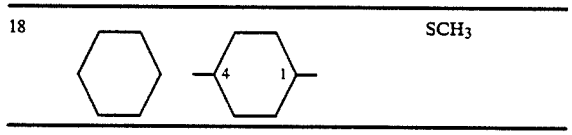 | SCH₃ |

| Example No. | (CH₂)ₘ | (CH₂)ₙ | R |
|---|---|---|---|
| 19 | | | CH₂—CH₂—CH=CH₂ |
| 20 | | | H |

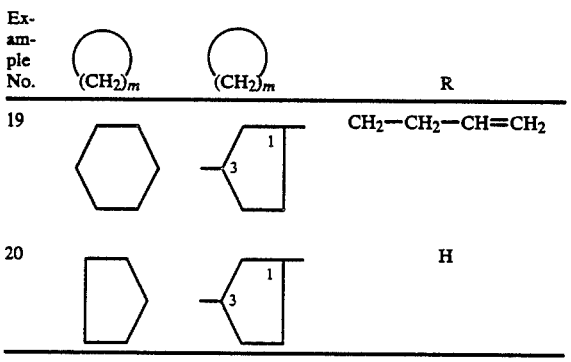

What is claimed is:

1. A pharmaceutical composition for inhibiting allergic conditions in a mammalian species comprising a pharmaceutically acceptable carrier and an effective amount of a compound of the formula wherein are cycloalkyl groups which may be the same or different, where m is an integer from 3 to 8 and n is an integer from 3 to 8; and R is H, lower alkyl, substituted alkyl including aralkyl, aryl, substituted aryl, lower alkenyl, or cycloalkyl;
including pharmaceutically acceptable salts thereof.

2. A composition of claim 1 wherein $(CH_2)_n$ in substituted at the 2, 3 or 4 position with $(CH_2)_m$.

3. A composition of claim 1 wherein m and n are each 6.

4. A composition of claim 3 wherein R is lower alkyl.

5. A composition of claim 4 wherein R is methyl.

6. A composition of claim 4 wherein R is 1,1-dimethylethyl.

7. The composition of claim 1 wherein said compound has the name 4-cyclohexyl-N-hydroxy-N-methylcyclohexane-carboxamide.

8. The composition of claim 1 wherein said compound has the name 4-cyclohexyl-N-(1,1-dimethylethyl)-N-hydroxy-cyclohexanecarboxamide.

9. A method of inhibiting $\Delta^5$-lipoxygenase which comprises administering to the circulatory system of a mammalian host an effective amount of a composition as defined in claim 1 or a pharmaceutically acceptable salt thereof.

10. The method of claim 9 wherein said composition is administered in an amount within the range of from about 1 to about 100 mg/kg.

11. A method for treating asthma in a mammalian species in need of such treatment, which comprises administering to a mammalian host an effective amount of a composition as defined in claim 1 or a pharmaceutically acceptable salt thereof.

* * * * *